United States Patent [19]
Mayo et al.

[11] Patent Number: 4,730,480
[45] Date of Patent: Mar. 15, 1988

[54] GAS CHROMATOGRAPH COLLECTION DEVICE AND PROCESS

[75] Inventors: Dana W. Mayo, Brunswick, Me.; Ronald M. Pike, Pelham, N.H.

[73] Assignee: Microscale Organic Laboratory Corporation, Newcastle, N.H.

[21] Appl. No.: 877,740

[22] Filed: Jun. 24, 1986

[51] Int. Cl.⁴ .......................................... G01N 31/08
[52] U.S. Cl. ...................................................... 73/23.1
[58] Field of Search ................ 73/23.1, 864.73; 55/67, 55/197, 386; 422/89

[56] References Cited

U.S. PATENT DOCUMENTS

| | | | |
|---|---|---|---|
| 2,119,288 | 5/1938 | Raymond | 73/864.73 |
| 2,284,147 | 5/1942 | Herrick | 73/864.73 |
| 3,011,336 | 12/1961 | Weiss | 73/863.12 |
| 3,778,975 | 12/1973 | Deans | 55/197 |
| 4,083,702 | 4/1978 | Hartigan et al. | 55/67 |
| 4,451,364 | 5/1984 | Higgins et al. | 55/386 |

Primary Examiner—Stewart J. Levy
Assistant Examiner—Hezron E. Williams
Attorney, Agent, or Firm—Thomas N. Tarrant

[57] ABSTRACT

Apparatus and a process for collecting the output of a gas chromatograph are disclosed in which a heat sinking adapter at the output port of a gas chromatograph is connected to a collection tube having bulbous enlargements for collecting condensate and a ground tapered end for making a tapered seal to a tapered throat in the adapter. A collection vial with a conical cavity and having the same tapered throat as the adapter accepts a transfer of the collection tube from the adapter and is suited for direct installation into a centrifuge. The disclosure is of particular interest in microscale preparative gas chromatography.

7 Claims, 5 Drawing Figures

GAS CHROMATOGRAPH COLLECTION DEVICE AND PROCESS

BACKGROUND OF THE INVENTION

1. Field of the Invention:

The present invention relates to containers and accessory connectors and processes for collecting the output of gas chromatographs and transferring said output to a further processing stage.

2. Relation to the Prior Art:

Gas chromatography involves the passing of chemical mixture samples in gaseous form through a chromatographic apparatus where the constituent components are spread out by delay factors inherent to their particular character. Knowing the delay characteristics for the different components, output collectors can be changed at the appropriate time intervals and their contents measured to determine what proportion of each component is in the original sample.

Inert gases such as helium or nitrogen are added to provide a flow medium or "carrier".

The output port of the chromatograph is usually connected to a collecting tube. A U-shaped tube is common since it allows condensate to drop to the bottom of the "U" with carrier gas flowing by it. There is usually some of the desired material passing on through the collecting tube with the carrier gas, either because it has not condensed or because the carrier gas has caught it up in bubbles and pushed it on out the open end. The condensate in the collection tube is recovered by various means, one of which is to remove the collection tube, place it in a centrifuge tube and drive the condensate from the collection tube by centrifuge action. Increasing interest in microscale preparative chromatography has placed a demand on increasing the sophistication of the steps dealing with the output of the chromatograph. In microscale operation, quantities are too small to allow for averaging out of descrepancies; the presenceof small amounts of contaminants are of particular concern. Precise control is a necessity.

SUMMARY OF THE INVENTION

The present invention provides three components of apparatus and appropriate process steps to assure precise control in the collection and transfer of gas chromatograph products. A metallic adapter connects a collection tube to the output port of a gas chromatograph using a tapered joint sealing the tube to the adapter. The collection tube has one or more enlarged annular portions for collecting condensate. A collection vial has a tapered throat matching the taper in the adapter so that the collection tube can be transferred from the adapter to the collection vial using the same joint taper.

Thus it is an object of the invention to provide a novel combination of a chromatagraph output port adapter and a collectiontube for gas chromatograph products.

It is a further object of the invention to provide a port adapter and a collection vial that both mate to the identical taper of a collection tube.

It is still a further object of the invention to provide a process for collecting the output of a gas chromatograph and transferring it to a further processing step with minimal loss or contamination.

Further object and features of the invention will become apparent upon reading the following description together with the drawing.

DESCRIPTION OF THE PREFERRED EMBODIMENTS

Additional information relative to the present invention and its use may be found in the book, *MICROSCALE ORGANIC LABORATORY*, by Dana W. Mayo, Ronald M. Pike and Samuel S. Butcher, published by John Wiley & Sons, 1986, which is herein incorporated by reference.

Figure 1:
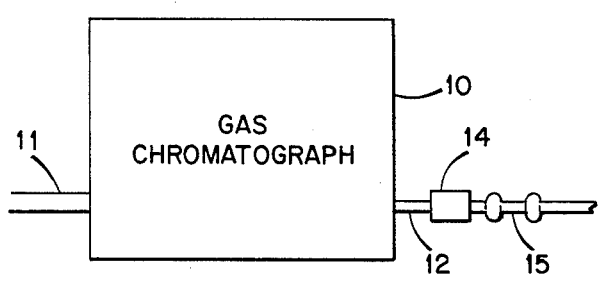
FIG. 1 is a diagramatic illustration of the invention partially in block form.

A gas chromatograph, 10, is depicted in block form in FIG. 1. Chromatograph 10 has input port 11, through which a sample mixture and carrier gas may be introduced, and output port 12. Port 12 may be a threaded male terminal of metal, glass or plastic pipe. Adapter 14 couples port 12 to collection tube 15. Port 12, adapter 14 and tube 15 are better illustrated in FIG. 2 drawn to the full size scale of actual components. The sizes are subject to variation and the particular examples given are for specific example noting that size and shape are not critical except as hereinafter specifically stated.

Figure 2:
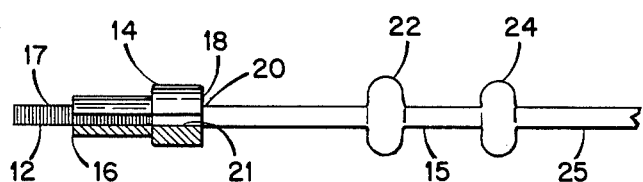
FIG. 2 is a front elevation of the invention partially in section including only the output port of the gas chromatograph.

In the example depicted by FIG. 2, port 12 and adapter 14 have 6-32 npt threads 17 with the female portion being first end 16 of adapter 14. Second end 18 of adapter 14 has female tapered joint 21 to receive a ground male tapered end 20 of collection tube 15. Adapter 14 is preferably made of a highly thermally conductive corrosion-resistant material such as stainless steel. By using a thermally conductive material and giving adapter 14 appreciable mass relative to adjacent components, significant heat sinking effect is produced; metallic materials have been found desirable. In the microscale analysis of primary interest, masses ranging from 5 grams to 30 grams have been found suitable for adapter 14. The heat sinking effect has produced an improvement in condensation rate of the desired output product.

In FIG. 2, the connection of adapter 14 to port 12 is adjustable since it is a screw thread connection. Other types of connections may be utilized depending on the output port of the specific chromatograph, but the adjustability is desirable. In use, collection tube 15 is seated tightly in seat 21 and then adapter 14 is threaded onto port 12 until tube 15 can be felt to make physical contact with port 12. Collection tube 15 may be made of glass or quartz and is preferably a straight tube ground to a taper at end 20 to form a sealing joint with adapter 14.

Collection tube 15 additionally has two annular enlargements 22 and 24 along its length to collect condensate out of the flow path of carrier gas. Annular rings 22 and 24 suitably have about twice the diameter of the rest of the tube 15, but neither the number or the diameter of the annular enlargements is critical. One annular enlargement can be sufficient and three or more can be utilized. The length of tube 15 must be enough to allow condensation and collection of the desired product, but is preferably short enough to install in a centrifuge as will be described hereinafter.

Far end 25 of tube 15 is an open end to allow the emission of carrier gas. In the event there are any toxic products involved, end 25 can be connected to tubing for transporting output gas to a safe containment or dispersal point.

Figure 3:
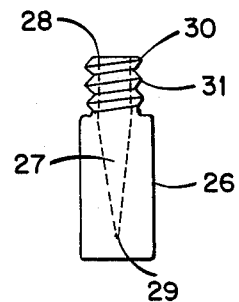
FIG. 3 is a front elevation of a glass collection vial in accordance with the invention.
Figure 4:
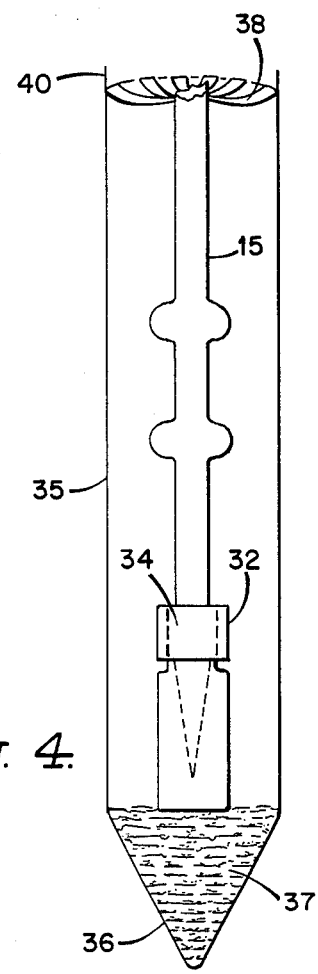
FIG. 4 is a front elevation of a centrifuge tube containing the assembled collection tube and collection vial according to the invention.

The third collection apparatus component of the invention is collection vial 26 depicted in FIGS. 3 and 4. The only limitation on the exterior size and shape of vial 26 is that it should fit into the holding cell of a centrifuge to be used. The inside of vial 26 has a conical cavity, 27, with the apex of the cone at the bottom of the vial. The top of vial 26 has tapered throat 28 connecting to cavity 27. Tapered throat 28 exactly matches tapered seat 21 of adapter 14 whereby tapered end 20 of tube 15 can be withdrawn from adapter 14 and joined sealingly to vial 26.

The invention is particularly useful in microscale preparative gas chromatography where the useful capacity for vial 26 falls in the range of 0.01 mL to 0.3 mL.

Vial 26 preferably has an external thread 30 at top end 31 so that it may be sealed with a cap for storage or transport. Other closure means may be used and a special cap 32 with aperture 34 can be used to assure a stronger seal of tube 15 to vial 26.

FIG. 4 illustrates the tube 15 assembled with vial 26 mounted in centrifuge tube 35. Cotton padding 37 in bottom 36 of tube 35 provides a cushioned support for vial 26, while spider 38 at top 40 of tube 35 gives lateral support to collection tube 15. The padding and support means are not critical and obvious substitutes may be used. Tube 35 serves as a holding cell for a centrifuge and will vary in accordance with the centrifuge.

Figure 5:
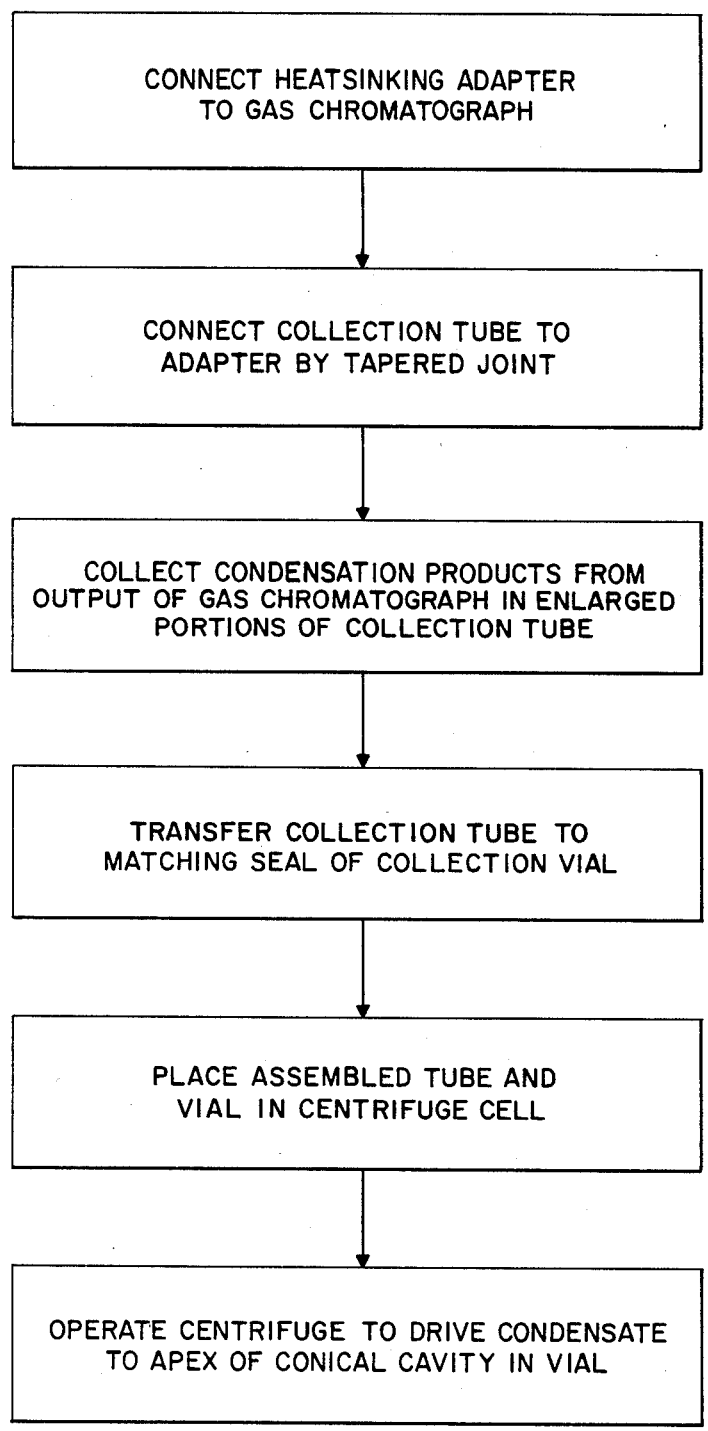
FIG. 5 is a flow chart of the inventive process.

The collection process of the invention is listed in flow chart, FIG. 5. Heatsinking adapter 14 is screwed to output port 12 of gas chromatograph 10. Ground tapered end 20 of collection tube 15 is sealed to adapter 14. The output product of the chromatograph is collected in enlarged portions 22, 24 of tube 15. Collection tube 15 is transferred to the matching seal of vial 26. The assembled collection tube and vial are installed in cell 35 of a centrifuge. The centrifuge is operated until the output product of the chromatograph is driven densely into apex 29 of vial 26.

After the collection process above, vial 26 may be removed from the centrifuge, tube 15 removed from the vial and the vial sealed with a cap.

While the invention has been described with respect to specific embodiments, obvious variations within the skill of the art are contemplated and it is intended to cover the invention as set forth within the scope of the following claims.

We claim:

1. Apparatus for collecting the output of a gas chromatograph comprising:
   a. a metallic adapter having a first end connectable to a carrier gas output port of a gas chromatograph and a second end mating with a collection tube in sealing relationship; and,
   b. a horizontal collection tube having at least on annular enlarged portion and an end for mating with said adapter in sealing relationship, whereby said collection tube can be seated firmly sealed with said second end and condensate forming in output gases of the chromatograph will be caught in the annular enlarged portion out of the path of carrier gas.

2. Apparatus for collecting the output of a gas chromatograph according to claim 1 wherein said first end is adjustable whereby, when the collection tube is firmly seated in said second end, said adapter can be adjusted to bring the end of said collection tube in direct contact with said output port of said chromatograph.

3. Apparatus for collecting the output of a gas chromatograph according to claim 1 further comprising a vial having a conical cavity and a mouth matching said second end whereby said collecting tube can be removed from said second end and sealed to the mouth of said vial, the assembly thus created being suitable for installation in a centrifuge.

4. Apparatus for collecting the output of a gas chromatograph according to claim 3 wherein said apparatus is designed for microscale preparative gas chromatogrphy with the capacity of the conical cavity in said vial being in the range of 0.01 mL to 0.3 mL.

5. Apparatus for collecting the output of a gas chromatograph according to claim 4 wherein said adapter is made of a noncorrosive metal having a mass in the range of 5 to 30 grams whereby said adapter acts as a heat sink aiding condensation of output products.

6. A process for handling the output of a gas chromatograph in microscale chromatography comprising:
   a. connecting a heatsinking adapter to the output port of a gas chromatograph;
   b. connecting a collection tube having annular enlargements to said adapter by means of a tapered glass-to-metal joint;
   c. receiving the output of said chromatograph in said tube collecting condensation products in said enlargements;
   d. transferring said tube to a collection vial having a matching taper in its throat for a second tapered joint;
   e. placing the assembled tube and vial in a centrifuge cell and operating the centrifuge so as to drive condensate from said enlargements into said vial with the denser portion at the bottom of said vial.

7. A process for handling the output of a gas chromatograph in microscale chromatography comprising:
   a. connecting a heatsinking adapter to a carrier gas output port of a gas chromatograph;
   b. connecting a collection tube having at least one annular enlargement to said adapter by a gastight joint;
   c. receiving the output of said chromatograph in said tube, collecting condensate products in said at least one annular enlargement;
   d. transferring said tube to a collection vial having a mating gas tight joint;
   e. placing the assembled tube and vial in a centrifuge cell; and,
   f. operating the centrifuge so as to drive condensate from said at least one annular enlargement into said vial with the denser portion at the bottom of said vial.

* * * * *